United States Patent [19]

Dietz et al.

[11] Patent Number: 4,994,227
[45] Date of Patent: Feb. 19, 1991

[54] METHOD FOR THE PREPARATION OF SUSTAINED RELEASED BOLUS FORMULATION

[75] Inventors: Joseph C. Dietz, Feasterville, Pa.; Richard B. Toothill, Warren, N.J.

[73] Assignee: American Cyanamid Company, Stamford, Conn.

[21] Appl. No.: 306,971

[22] Filed: Feb. 3, 1989

Related U.S. Application Data

[63] Continuation of Ser. No. 12,262, Feb. 19, 1987, abandoned, which is a continuation-in-part of Ser. No. 837,636, Mar. 10, 1986, abandoned.

[51] Int. Cl.$^5$ .................. B29C 45/00; B29C 45/72; A01N 25/34
[52] U.S. Cl. ..................... 264/328.16; 264/328.1; 264/328.18; 424/405; 424/438; 514/964
[58] Field of Search ........... 264/328.1, 328.16, 328.18; 514/964, 965; 424/476, 457, 459, 405, 438; 604/890; 426/512

[56] References Cited

U.S. PATENT DOCUMENTS

| | | | |
|---|---|---|---|
| 3,432,592 | 3/1969 | Speiser | 264/328.18 |
| 4,007,258 | 2/1977 | Cohen et al. | 514/965 |
| 4,166,107 | 8/1979 | Miller et al. | 424/405 |
| 4,181,710 | 1/1980 | Dannelly et al. | 424/476 |
| 4,326,522 | 4/1982 | Guerrero | 604/57 |
| 4,665,100 | 5/1987 | Ludwig | 514/778 |

*Primary Examiner*—Mary Lynn Theisen
*Attorney, Agent, or Firm*—John W. Hogan, Jr.

[57] ABSTRACT

The invention is an injection molding method for the preparation of sustained release boluses which are useful for administration of insect growth regulators or other veterinary compositions to animals.

5 Claims, No Drawings

4,994,227

METHOD FOR THE PREPARATION OF SUSTAINED RELEASED BOLUS FORMULATION

This is a continuation of application, U.S. Ser. No. 012,262, filed Feb. 19, 1987, now abandoned, which is a continuation-in-part of U.S. application Ser. No. 837,636, filed Mar. 10, 1986, now abandoned.

BACKGROUND OF THE INVENTION

The use of slow release bolus formulations which provide animals with small daily dosages of materials over extended periods of time has been shown to be an effective alternative to repeated treatments.

While considerable research has been undertaken to provide novel bolus compositions utilizing various materials to obtain the desired release rates, such as those described in British Patent Application No. GB 2077103A and U.S. Pat. No. 4,444,927, which employ biodegradable polymers and polydioxanones, respectively, relatively little research has been reported on specific manufacturing processes suitable for their preparation or the effect of the process used on the performance of the bolus.

U.S. Pat. No. 4,166,107 describes effective, sustained-release bolus formulations, containing insect growth regulators with a mixture of a wax, a fat and barium sulfate, useful for the control of arthropods in manure, that are prepared by atmospheric molding or by compression molding.

It is an object of this invention to provide an injection-molding method for the preparation of sustained release bolus formulations containing insect growth regulators or other veterinary compositions, which is suitable for the manufacture of commercial quantities of sustained release boluses.

It is another object of this invention to provide improved, uniform performance of sustained release bolus formulations by utilizing the method of the invention.

SUMMARY OF THE INVENTION

The invention is a method for the preparation of sustained release bolus formulations which utilizes injection molding. The boluses are administered to animals orally. The process of the invention is injecting a molten dry blend or pelletized dry blend containing 1% to 20% on a weight basis active ingredient; 1.0% to 40% on a weight basis wax or a mixture of waxes; 0% to 23% on a weight basis fat and 20% to 85% on a weight basis of high-density, pharmacologically and pharmaceutically acceptable filler or weighting agent into a mold, cooling the mold to solidify the bolus and removing the molded bolus from the mold.

Active ingredients suitable for administration in sustained release boluses prepared by the method include insect growth regulators such as methoprene, diflubenzuron and the like; antibiotics such as avoparcin, sulfamethazine, tetracycline, tylosin, and the polyether ionophores such as monensin, salinomycin, lasalocid, and maduramicin; anthelmintic agents, such as tetramisol, levamisol, ivermectin, phenothiazene as well as other veterinary compositions for which sustained release bolus administration would be desirable.

Paraffin and microcrystalline animal, mineral and vegetable waxes, such as carnauba wax, montan wax, lignite, ozocerite, ceresin, utah, peat, bayberry and candelilla waxes and mixtures thereof, are exemplary of the waxes which may be employed in the injection molding method of the present invention, alone or in combination with mono, di-, or tri- glycerides having HLB values of less than 2.0 and melting points above ambient temperatures such as glycerol monostearate.

Fillers and weighting agents which have utility in the method of this invention include but are not limited to barium sulfate, barite, calcium sulfate, calcium carbonate, silicas, wollastonite, zeolites, iron ore, iron filings and the like. Many of these fillers and weighting agents are commercially available in both highly purified forms and natural grades which are acceptable and suitable for pharmaceutical use. Preferred fillers for use in the method of the invention include purified barium sulfate and naturally occuring barite fines. Barite fines are a naturally occuring source of barium sulfate containing about 92% $BaSO_4$ having a specific gravity of about 4.25 and a bulk density of about 150 pounds per cubic foot, and having a particular size range such that 85% to 90% (cumulative weight %) is retained on a 325 mesh screen.

The preparation of sustained release bolus formulations is readily accomplished by blending on a weight basis 1% to 20% active ingredient; 1.0% to 40% wax or a mixture of waxes; 0% to 23% fat; and 20% to 85% of a high density, pharmacologically and pharmaceutically acceptable filler, in a temperature range below the melting point of the wax or mixture. The blend may be used in the injection molding step as is, or the blend may be pelletized or flaked using an extruder or flaker and the resulting pellets or flakes used for injection molding.

After blending, the mixture is discharged and either transferred to a pelletizing extruder or directly charged into the injection molder. If pelletizing is desired for improved homogeneity, the mixture may be pelletized utilizing a three-stage temperature profile comprising a feed section maintained at a temperature below the melting point of the wax or mixture of waxes, a hot transition section maintained at a temperature above the melting point of the wax or mixture of waxes and stearates, and a metering section maintained at a temperature below the melting point of the wax or mixture of waxes and stearates employing with a straight-through die equipped with a breaker plate, the die equipped breaker plate assembly being maintained at a temperature range which is similar to the range of the metering section. The resulting extruded material is air cooled and cut into pellets of the desired size. Improved homogeneity may also be obtained by flaking the blend of active ingredient, waxes, fat and filler, by prilling, wax granulating with commercially available equipment or any method known to produce better homogeneity.

The resulting pellets and/or dry blend materials are transferred to an injection molding system which is operated with a three stage temperature profile similar to that employed for pelletization; i.e, a feed phase below the mixture softening point, a transition phase above the softening point, and an injection phase wherein the mixture is injected into a mold at a temperature below the softening point of the blend. The mold is cooled to solidify the bolus. Boluses produced are then removed from the mold and packaged.

While the above process may be carried out satisfactorily with a variety of fillers and weighting agents as previously described above, barite fines are preferred. The use of barite fines in the process has several advantages over the use of purified USP grade barium sulfate with regard to hardness of bolus, and methanol erosion rate of the bolus.

During the processing of the mixtures containing waxes and fats and waxes, the use of barite fines produces less tacky and more easily handled solid mixtures.

A further advantage of the injection molding process of the invention is that it avoids the need for cryogenic grinding of the solid mixture or the use of additional lubricants frequently required in other methods, such as tablet pressing of solids. Still another advantage is that recycling of particles retained on 100 mesh is avoided. Tablet pressing requires 100 mesh material for pressing since use of a > 100 mesh mix results in faster release of active agents from the bolus.

The invention is further illustrated by the following non-limiting examples.

EXAMPLE 1

Preparation of a sustained release bolus formulation containing diflubenzuron.

A sustained release bolus formulation of the insect growth regulator diflubenzuron is prepared by a mixing on a weight basis 10.31% diflubenzuron (98% pure) 13.45% glycerol monostearate, 4.49% carnauba wax and 71.75% barite mined in Battle Mountain, Nev., in a blender maintained at about 80° C. for about 10 minutes.

After blending, the mixture is discharged and transferred to a pelletizing extruder and/or directly charged to the injection molder.

In the case of direct feeding of the dry blend, a feeding system, (e.g, by VIBRA-SCREW®, Totowa, N.J.), may be used to transfer the material to an injection molding system utilizing a hot runner system and a shut-off nozzle. Operating conditions for the injection molding process include feeding the blend into the screw at a temperature below 60° C., gradually heating the blend to a temperature above its softening point and forcing the softened blend into the mold. The mold is cooled to solidify the bolus and the bolus is removed, weighing about 50 grams, having a density of about 2.4 g/cc and a hardness as measured on a DELAMAR press, (Delamar Co., Elk Grove Village, Ill.), of about 75 kg.

If pelletizing is carried out before the injection molding, the blended mixture is pelletized using a bell-shaped temperature profile comprising a cooled feeding section (50°-60° C.), a hot transition section (100°-110° C.) and a cooled metering section (50°-60° C.) with a straight-through ⅜ inch die equipped with a 20 mesh screen breaker plate. The die temperature is maintained at 55°-60° C. Resulting extruded rope is air cooled (by an air stream blowing at the die opening) and cut into ¼" pellets with a hot face cutter.

EXAMPLES 1-9

Preparation of sustained release bolus formulation

Utilizing the procedure of Example 1 and varying the quantity of barite, glycerol monostearate and carnauba wax yields sustained release bolus formulations listed in Table I below:

TABLE 1

| Bolus Formulation | Glycerol Monostearate (wt) Carnauba Wax (wt) | Barite (wt) Total Wax (wt) | Physical Properties | |
|---|---|---|---|---|
| | | | Weight (g) | Density (g/cc) |
| Compression Molded | 3/1 | 4/1 | 50 | 2.38 |
| Atmospheric Molded | 3/1 | 4/1 | 50 | 2.38 |
| Example No. | | | | |
| 1 | 3/1 | 4/1 | 50 | 2.38 |
| 2 | 3/1 | 5/1 | 54 | 2.50 |
| 3 | 3/1 | 6/1 | 56 | 2.60 |
| 4 | 4/1 | 4/1 | 50 | 2.38 |
| 5 | 2.5/1 | 4/1 | 50 | 2.38 |
| 6 | 2/1 | 4/1 | 50 | 2.38 |
| 7 | 1/1 | 4/1 | 50 | 2.38 |
| 8 | 7.5/1 | 3.94/1 | 48 | 2.20 |
| 9 | 4/1 | 4/1 | 48 | 2.20 |

EXAMPLE 10

Erosion of bolus formulations

Weighed boluses are mounted on a stirring rod of a standard dissolution apparatus and placed in a container containing absolute methanol, maintained at 37° C. The apparatus is then engaged at a stirring speed of 150 rpm. Stirring is continued for six hours, at which time the boluses are removed. The loose material is removed using slight abrasion and the remainder of the bolus weighed. Results are reported in Table II below as percent weight loss of the original weight.

TABLE II

| Comparative Erosion | |
|---|---|
| Bolus | Erosion (wt %) |
| Compression Molded | 46.9 |
| Atmospheric Molded | 38.7 |
| Example No. | |
| 1 | 30.3 |
| 2 | 27.9 |
| 3 | 37.6 |
| 4 | 32.3 |
| 5 | 28.5 |
| 6 | 23.0 |
| 7 | 19.0 |

EXAMPLE 11

Preparation of sustained release bolus formulations containing the antibiotic avoparcin Utilizing the procedure of Example 1, 50 g-boluses containing on a weight basis 1% to 18% avoparcin; 10% to 18% montan acid wax; 10% to 18% carnauba wax; and 52% to 66% barite are prepared, having barite to total wax weight ratios ranging from 1.14:1 to 3:1. The amount of avoparcin released from these boluses over time is determined in a standard dissolution apparatus utilizing a standard synthetic rumen saliva, which is a buffer solution comprised of $NaHCO_3$ (9.8 g/l); KCl (0.57 g/l); $CaCl_2$ (0.04 g/l); $NaHPO_4.12H_2O$ (9.3 g/l); NaCl (0.47 g/l) and $MgSO_4.7H_2O$ (0.12 g/l) at pH 6.5.

The results of these experiments, which are summarized in Table III below, demonstrate the varying release of avoparcin obtained with several of the boluses prepared above.

TABLE III

In Vitro Release Rate Of Avoparcin From 50 g Boluses (mg/day)

| Barite/Wax Ratio | 3:1 | 1.14:1 | 1.4:1 | 2.15:1 |
|---|---|---|---|---|
| Avoparcin (% bolus wt) | 12.7 | 17.3 | 15.2 | 13.2 |
| Days of Study | Active Release (mg/day) | | | |
| 1 | 190 | 402 | 215 | 255 |
| 7 | 200 | 159 | 185 | 243 |
| 14 | 106 | 50 | 110 | 210 |
| 28 | 50 | — | 164 | — |

What is claimed is:

1. An injection molding method for the preparation of sustained release bolus formulations comprising the steps of (a) feeding a dry blend or pelletized dry blend consisting of 1% to 20% on a weight basis of active ingredient; 1.0% to 40% on a weight basis of wax or a mixture of waxes; 0% to 23% on a weight basis of fat; and 20% to 85% of a high-density, pharmacologically and pharmaceutically acceptable filler into a screw at a temperature below about 60° C., gradually heating the blend to a temperature above its softening point and forcing the softened blend into a mold, (b) cooling the mold to solidify the bolus and (c) removing the molded bolus from the mold.

2. A method according to claim 1, wherein the active ingredient is an insect growth regulator, antibiotic, or an anthelmintic.

3. A method according to claim 2, wherein the insect growth regulator is diflubenzuron.

4. A method according to claim 2, wherein the antibiotic is avoparcin, sulfamethazine, tetracycline, tylosin or a polyether ionophore.

5. A method according to claim 2, wherein the anthelmintic agent is levamisol, tetramisol, ivermectin or phenothiazine.

* * * * *